imary Examiner—Donald G. Daus
United States Patent [19]

Okamoto et al.

[11] 4,104,392
[45] Aug. 1, 1978

[54] N²-NAPHTHALENESULFONYL-L-ARGININAMIDES AND THE PHARMACEUTICALLY ACCEPTABLE SALTS THEREOF, AND ANTITHROMBOTIC COMPOSITIONS AND METHODS EMPLOYING THEM

[75] Inventors: Shosuke Okamoto, 15-18, Asahigaoka 3-chome, Tarumi-ku, Kobe-shi, Hyogo, Japan; Akiko Hijikata, Kobe, Japan; Ryoji Kikumoto, Machida, Japan; Yoshikuni Tamao, Yokohama, Japan; Kazuo Ohkubo, Machida, Japan; Tohru Tezuka, Yokohama, Japan; Shinji Tonomura, Tokyo, Japan

[73] Assignees: Mitsubishi Chemical Industries Ltd., Tokyo; Shosuke Okamoto, both of Japan

[21] Appl. No.: 728,051

[22] Filed: Sep. 30, 1976

Related U.S. Application Data

[60] Continuation-in-part of Ser. No. 671,436, Mar. 29, 1976, Pat. No. 4,066,758, and Ser. No. 671,568, Mar. 29, 1976, Pat. No. 4,049,645, each is a division of Ser. No. 622,390, Oct. 14, 1975, abandoned.

[30] Foreign Application Priority Data

| Nov. 8, 1974 | [JP] | Japan | 49/128774 |
| Nov. 8, 1974 | [JP] | Japan | 49/128775 |
| Nov. 29, 1974 | [JP] | Japan | 49/136695 |
| Nov. 29, 1974 | [JP] | Japan | 49/136697 |
| Feb. 25, 1975 | [JP] | Japan | 50/023268 |
| Feb. 26, 1975 | [JP] | Japan | 50/023635 |
| Mar. 5, 1975 | [JP] | Japan | 50/026768 |
| Mar. 11, 1975 | [JP] | Japan | 50/029357 |
| Mar. 11, 1975 | [JP] | Japan | 50/029358 |

[51] Int. Cl.² ............... A61K 31/47; A61K 31/40; C07D 217/26; C07D 209/44

[52] U.S. Cl. .............. 424/258; 260/287 D; 260/287 T; 260/287 G; 260/283 SA; 260/326.1; 260/326.11 R; 424/274

[58] Field of Search ........ 260/283 SA, 287 D, 287 T, 260/326.1, 236.11 R; 424/258, 274

[56] References Cited

U.S. PATENT DOCUMENTS

| 3,978,045 | 8/1976 | Okamoto et al. | 260/239 B |
| 4,049,645 | 9/1977 | Okamoto et al. | 260/239 B |
| 4,062,963 | 12/1977 | Okamoto et al. | 424/267 |
| 4,066,759 | 1/1978 | Okamoto et al. | 424/244 |

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

N²-naphthalenesulfonyl-L-argininamides and the pharmaceutically acceptable salts thereof have been found to be effective as pharmaceutical agents for the inhibition and suppression of thrombosis.

12 Claims, No Drawings

$N^2$-NAPHTHALENESULFONYL-L-ARGININAMIDES AND THE PHARMACEUTICALLY ACCEPTABLE SALTS THEREOF, AND ANTITHROMBOTIC COMPOSITIONS AND METHODS EMPLOYING THEM

CROSS REFERENCE TO RELATED APPLICATIONS

This application is a continuation in part of applications Ser. No. 671,436 Mar. 29, 1976, now U.S. Pat. No. 4,066,758, and Ser. No. 671,568 filed Mar. 29, 1976, now U.S. Pat. No. 4,049,645, which in turn are divisionals of application Ser. No. 622,390 filed Oct. 14, 1975, now abandoned.

BACKGROUND OF THE INVENTION

1. Field of the Invention

This invention relates to the discovery of certain new and useful $N^2$-naphthalenesulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The $N^2$-(p-tolylsulfonyl)-L-arginine esters have been found to be one type of agent which can be used and these have been found to be effective in dissolving blood clots. (U.S. Pat. No. 3,622,615, issued Nov. 23, 1971) One family of compounds which have been found to be particularly useful as highly specific inhibitors of thrombin for the control of thrombosis is the $N^2$-dansyl-L-arginine ester or amide. (Our pending U.S. application Ser. No. 496,939, filed Aug. 13, 1974 now U.S. Pat. No. 3,978,045) However, there is a continuing need for a highly specific inhibitor on thrombin for the control of thrombosis, which exhibits lower toxicity.

SUMMARY OF THE INVENTION

It has now been discovered that $N^2$-naphthalenesulfonyl-L-argininamides exhibit antithrombotic activity and even lower toxicity levels at the same relative potencies, as compared with the $N^2$-dansyl-L-arginine ester or amide. The compounds of this invention can be represented by the formula (I):

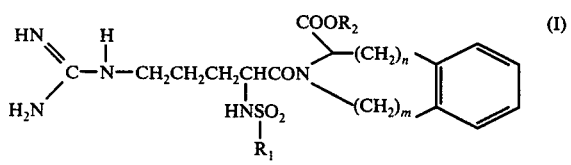

wherein $R_1$ is selected from the group consisting of naphthyl, 5,6,7,8-tetrahydronaphthyl and naphthyl substituted with at least one substituent selected from the group consisting of halo, nitro, cyano, hydroxy, $C_1$–$C_{10}$ alkyl, $C_1$–$C_{10}$ alkoxy and $C_2$–$C_{20}$ dialkylamino; $R_2$ is selected from the group consisting of hydrogen, $C_1$–$C_{10}$ alkyl, $C_6$–$C_{10}$ aryl and $C_7$–$C_{12}$ aralkyl; $m$ is an integer of 0, 1 or 2; $n$ is an integer of 0, 1 or 2; and $m+n$ is an integer of 1 or 2. Also encompassed within this invention are pharmaceutically acceptable salts thereof.

This invention also relates to a method for inhibiting activity and suppressing activation of thrombin in vivo, which comprises introducing into a living body a pharmaceutically effective amount of an $N^2$-naphthalenesulfonyl-L-argininamide or the pharmaceutically acceptable salt thereof.

DETAILED DESCRIPTION OF THE PREFERRED EMBODIMENTS

This invention relates to a group of $N^2$-naphthalenesulfonyl-L-argininamides of the formula (I):

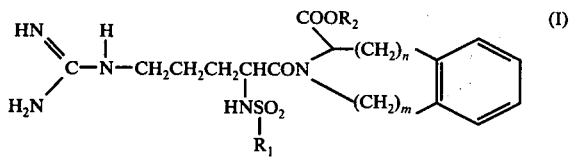

wherein $R_1$ is naphthyl, such as 1-naphthyl and 2-naphthyl, 5,6,7,8-tetrahydronaphthyl, such as 5,6,7,8-tetrahydro-1-naphthyl and 5,6,7,8-tetrahydro-2-naphthyl, or naphthyl substituted with at least one substituent selected from the group consisting of halo, such as fluoro, chloro, bromo and iodo, nitro, cyano, hydroxy, alkyl of 1–10 (preferably 1–5) carbon atoms, such as methyl, ethyl, propyl, isopropyl, butyl, isobutyl or the like, alkoxy of 1–10 (preferably 1–5) carbon atoms, such as methoxy, ethoxy, propoxy, isopropoxy, butoxy, sec-butoxy, tert-butoxy, pentyloxy or the like, and dialkylamino of 2–20 (preferably 2–10) carbon atoms, such as dimethylamino, diethylamino, N-methyl-N-ethylamino or the like; $R_2$ is hydrogen, alkyl of 1–10 (preferably 1–6) carbon atoms, such as methyl, ethyl, propyl, butyl, tert-butyl, hexyl, octyl, decyl or the like, $C_6$–$C_{10}$ aryl such as phenyl or naphthyl, and preferably phenyl, or aralkyl of 7–12 (preferably 7–10) carbon atoms, such as benzyl, phenethyl or the like; $m$ is an integer of 0, 1 or 2; $n$ is an integer of 0, 1 or 2; and $m+n$ is an integer of 1 or 2.

Suitable illustrations of $R_1$ in the above formula (I) are 1-naphthyl, 2-naphthyl, 5,6,7,8-tetrahydro-1-naphthyl, 5,6,7,8-tetrahydro-2-naphthyl, 6-methyl-2-naphthyl, 6-methyl-1-naphthyl, 7-methyl-1-naphthyl, 7-methyl-2-naphthyl, 6-ethyl-2-naphthyl, 6,7-dimethyl-1-naphthyl, 6,7-dimethyl-2-naphthyl, 6-isopropyl-2-naphthyl, 5-chloro-1-naphthyl, 6-chloro-2-naphthyl, 6-bromo-1-naphthyl, 5-hydroxy-1-naphthyl, 7-hydroxy-2-naphthyl, 5-dimethylamino-1-naphthyl, 5-dimethylamino-2-naphthyl, 5-diethylamino-1-naphthyl, 6-dimethylamino-1-naphthyl, 6-dimethylamino-2-naphthyl, 5-methoxy-1-naphthyl, 6-methoxy-2-naphthyl, 7-methoxy-2-naphthyl, 4,6-dimethoxy-2-naphthyl, 6,7-dimethoxy-2-naphthyl and 6,7-diethoxy-2-naphthyl.

Suitable $R_2$ groups in the above formula (I) are hydrogen, methyl, ethyl and tert-butyl.

The

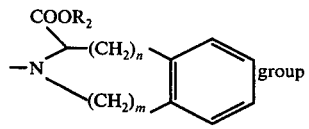

group in the above formula (I) includes

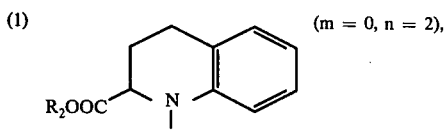

(1)                          (m = 0, n = 2), (2) 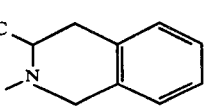 (m = 1, n = 1), (3) 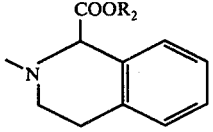 (m = 2, n = 0), (4) 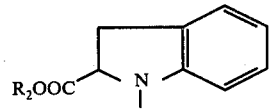 (m = 0, n = 1), and (5) 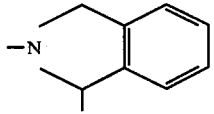 (m = 1, n = 0).

Suitable

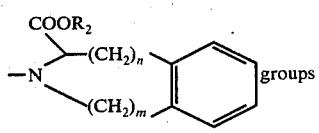 groups are 2-carboxy-1,2,3,4-tetrahydro-1-quinolyl

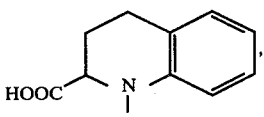, 3-carboxy-1,2,3,4-tetrahydro-2-isoquinolyl

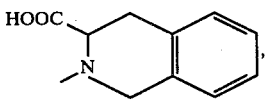, 1-carboxy-1,2,3,4-tetrahydro-2-isoquinolyl

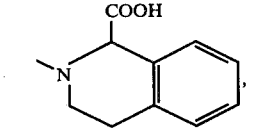, 2-carboxy-1-indolinyl

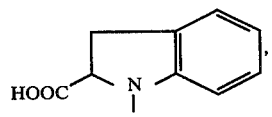

and 1-carboxy-2-isoindolinyl

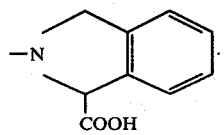.

Especially preferred are 3-carboxy-1,2,3,4-tetrahydro-2-isoquinolyl and 1-carboxy-2-isoindolinyl.

Illustrative of suitable $N^2$-naphthalenesulfonyl-L-argininamides of sufficient activity are the following:

2-[$N^2$-(6,7-dimethoxy-2-naphthalenesulfonyl)-L-arginyl]-1,2,3,4-tetrahydroisoquinoline-3-carboxylic acid 2-[$N^2$-(6,7-dimethoxy-2-naphthalenesulfonyl)-L-arginyl] isoindoline-1-carboxylic acid 2-[$N^2$-(7-methoxy-2-naphthalenesulfonyl)-L-arginyl] isoindoline-1-carboxylic acid 2-[$N^2$-(7-methyl-2-naphthalenesulfonyl)-L-arginyl] isoindoline-1-carboxylic acid The pharmaceutically acceptable salts of the above compounds are of course also included within the scope of this invention.

The above compounds are intended only to illustrate the variety of structures which can be used in the process of this invention, and the above listing is not to be construed as limiting the scope of the invention.

For the preparation of the compounds of this invention, various methods can be employed depending upon the particular starting materials and/or intermediates involved.

Successful preparation of these compounds is possible by way of several synthetic routes which are outlined below.

(a) Condensation of an L-argininamide with a naphthalenesulfonyl halide

This process may be illustrated as follows:

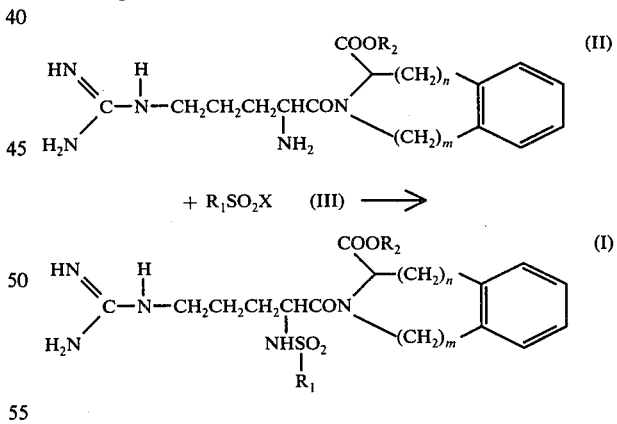

In the above formulas, $R_1$, $R_2$, $m$ and $n$ are as defined herein above, and X is halogen.

The $N^2$-naphthalenesulfonyl-L-argininamide (I) is prepared by the condensation of an L-argininamide (II) with a substantially equimolar amount of a naphthalenesulfonyl halide (III), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include chloroform, benzene-diethyl ether, diethyl ether-water and dioxane-water.

After the reaction is complete, the formed salt is extracted with water, and the solvent is removed by such standard means as evaporation under reduced pressure to give the $N^2$-naphthalenesulfonyl-L-argininamide (I), which can be purified by trituration or recrystallization from a suitable solvent, such as diethyl ether-tetrahydrofuran, diethyl ether-methanol, water-ethanol and water-methanol, or may be chromatographed on silica gel.

The L-argininamides (II) starting materials required for the condensation reaction can be prepared by protecting the guanidino and α-amino groups of the L-arginine via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine with a corresponding secondary amine by such a conventional process as the acid chloride method, azide method, mixed anhydride method, activated ester method or carbodiimide method, and thereafter selectively removing the protective group.

(b) Removal of the $N^G$-substituent from an $N^G$-substituted-$N^2$-naphthalenesulfonyl-L-argininamide This process may be illustrated as follows:

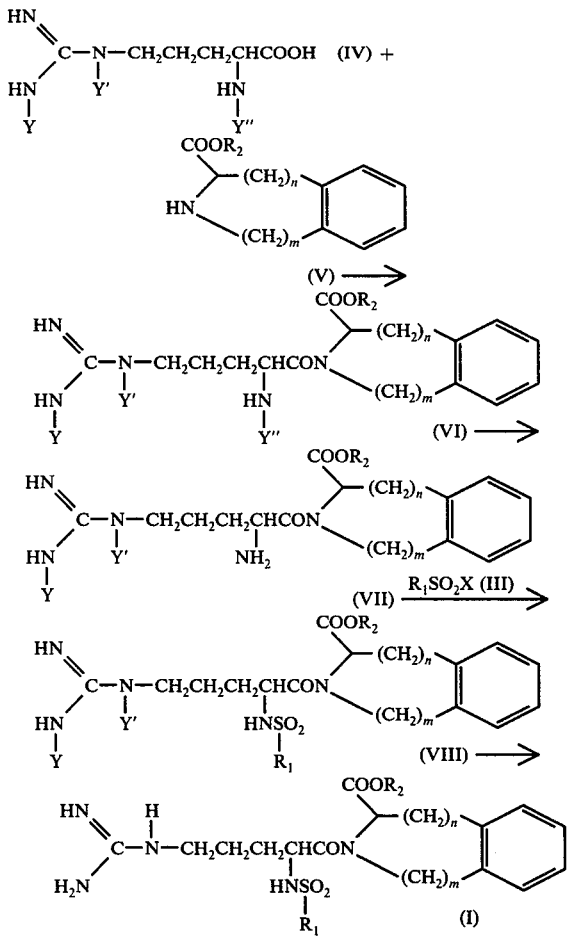

In the above formulas, $R_1$, $R_2$, X, m and n are as defined herein above; Y" is a protective group for the amino group, such as benzyloxycarbonyl or tertbutoxycarbonyl; and Y and Y' are hydrogen and protective groups for the guanidino group, such as nitro, tosyl, trityl, oxycarbonyl or the like. At least one of Y and Y' is a protective group for the guanidino group.

The $N^2$-naphthalenesulfonyl-L-argininamide (I) is prepared by removing the $N^G$-substituent from an $N^G$-substituted-$N^2$-naphthalenesulfonyl-L-argininamide (VIII) by means of acidolysis or hydrogenolysis. The acidolysis is generally effected by contacting the $N^G$-substituted-$N^2$-naphthalenesulfonyl-L-argininamide (VIII) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of $-10°$ to 100° C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-naphthalenesulfonyl-L-argininamides (I), which can be easily converted to a free amide by neutralization. The removal of the nitro group and the oxycarbonyl group, e.g., benzyloxycarbonyl, p-nitrobenzyloxycarbonyl, is readily accomplished by the hydrogenolysis. The hydrogenolysis is effected in a reaction-inert solvent, e.g., methanol, ethanol, tert-butanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours.

The hydrogen pressure is not critical, and atmospheric pressure is sufficient.

The $N^2$-naphthalenesulfonyl-L-argininamides (I) are isolated by filtration of the catalyst followed by evaporation of the solvent.

The $N^2$-naphthalenesulfonyl-L-argininamides can be purified in the same manner as described above.

The $N^G$-substituted-$N^2$-naphthalenesulfonyl-L-argininamides (VIII) starting materials can be prepared by condensing an $N^G$-substituted-$N^2$-substituted L-arginine (IV) (generally the $N^2$-substituent is a protective group for the amino group, such as benzyloxycarbonyl, tert-butoxycarbonyl, or the like) and a corresponding secondary amine (V) via the azide method, mixed anhydride method, activated ester method, carbodiimide method or the like, selectively removing only the $N^2$-substituent of an $N^G$-substituted-$N^2$-substituted L-argininamide (VI) by means of catalytic hydrogenolysis or acidolysis, and then condensing the thus obtained $N^G$-substituted-L-argininamide (VII) with a naphthalenesulfonyl halide (III), preferably a chloride in the presence of a base in a solvent. These reaction conditions are as described above in the condensation of an L-argininamide with a naphthalenesulfonyl halide, and the removal of the $N^G$-substituent from an $N^G$-substituted-$N^2$-naphthalenesulfonyl-L-argininamide.

(c) Condensation of an $N^2$-naphthalenesulfonyl-L-arginyl halide with an amine

This process may be illustrated as follows:

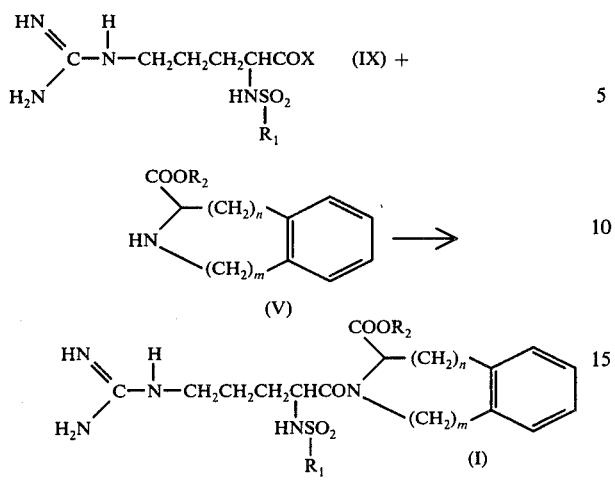

(IX) +

(V)

(I)

In the above formulas, $R_1$, $R_2$, X, m and n are as defined herein above.

The $N^2$-naphthalenesulfonyl-L-argininamide (I) is prepared by the condensation of an $N^2$-naphthalenesulfonyl-L-arginyl halide (IX), preferably a chloride with at least an equimolar amount of a secondary amine (V). The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-naphthalenesulfonyl-L-arginyl halide (IX). Preferred condensation reaction temperatures are in the range of from $-10°$ C to room temperature. The reaction time is not critical, but varies with the secondary amine (V) employed. In general, a period of from 5 minutes to 10 hours is operable.

The obtained $N^2$-naphthalenesulfonyl-L-argininamide can be isolated and purified in the same manner as described above.

The $N^2$-naphthalenesulfonyl-L-arginyl halide (IX) starting materials required for the condensation reaction can be prepared by reacting an $N^2$-naphthalenesulfonyl-L-arginine with at least an equimolar amount of a halogenating agent such as thionyl chloride, phosphorous oxychloride, phosphorus trichloride, phosphorous pentachloride or phosphorus tribromide. The halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-naphthalenesulfonyl-L-arginine.

Preferred reaction temperatures are in the range of $-10°$ C to room temperature. The reaction time is not critical, but varies with the halogenating agent and reaction temperature. In general, a period of 15 minutes to 5 hours is operable.

(d) Guanidylation of an $N^2$-naphthalenesulfonyl-L-ornithinamide or an acid addition salt thereof This process may be illustrated as follows:

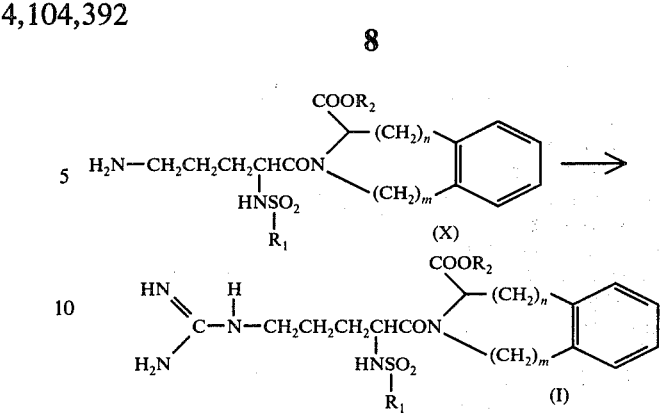

(X)

(I)

In the above formulas, $R_1$, $R_2$, m and n are as defined herein above.

The $N^2$-naphthalenesulfonyl-L-argininamide (I) is prepared by guanidylating an $N^2$-naphthalenesulfonyl-L-ornithinamide (X) with an ordinary guanidylating agent such as an O-alkylisourea, S-alkylisothiourea, 1-guanyl-3,5-dimethylpyrazole or carbodiimide. The preferred guanidylating agents are the O-alkylisourea and the S-alkylisothiourea.

The guanidylation of the $N^2$-naphthalenesulfonyl-L-ornithinamide (X) with the O-alkylisourea or S-alkylisothiourea is generally effected in a solvent in the presence of a base at a temperature of from 0° C to the boiling temperature of the solvent for a period of from 30 minutes to 50 hours.

Examples of the preferred bases are triethylamine, pyridine, sodium hydroxide and sodium methoxide.

The base is used in an amount of 0.01 to 0.1 equivalent to the $N^2$-naphthalenesulfonyl-L-ornithinamide.

Examples of the preferred solvents are water, water-ethanol and water-dioxane.

After the reaction is complete, the $N^2$-naphthalenesulfonyl-L-argininamide (I) is isolated by evaporation of the solvent followed by removal of the excess base and the formed salt by a water wash.

It is well recognized in the art that an ester derivative of the $N^2$-naphthalenesulfonyl-L-argininamide (I) wherein $R_2$ is alkyl, aryl or aralkyl, can be prepared from a carboxylic acid derivative of the $N^2$-naphthalenesulfonyl-L-argininamide wherein $R_2$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-naphthalenesulfonyl-L-argininamide (I) of this invention forms acid addition salts with any of a variety of inorganic and organic acids. Some of the $N^2$-naphthalenesulfonyl-L-argininamide containing a free carboxy group, wherein $R_2$ is hydrogen, forms salts with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-naphthalenesulfonyl-L-argininamides, and the salts thereof of this invention are characterized by highly specific inhibitory activity against thrombin as well as by their substantial lack of toxicity, and therefore these compounds are useful in the determination of thrombin in blood as diagnostic reagents, and/or for the medical control or prevention of thrombosis.

The antithrombotic activity of the $N^2$-naphthalenesulfonyl-L-argininamide of this invention was compared with that of a known antithrombotic agent, $N^2$-(p-tolysulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds. The antithrombotic activity of the compounds of this invention is shown in terms of "concentration required to prolong the coagulation time by a factor of two" which is the concentration of an active ingredient required to prolong the normal coagulation time 50–55 seconds to 100–110 seconds.

The concentrations required to prolong the coagulation time by a factor of two for 2-[$N^2$-(6,7-dimethoxy-2-naphthalenesulfonyl)-L-arginyl]-1,2,3,4-tetrahydroisoquinoline-3-carboxylic acid and 2-[$N^2$-(6,7-dimethoxy-2-naphthalenesulfonyl)-L-arginyl]isoindoline-1-carboxylic acid were 2 $\mu$ M and 1.5 $\mu$ M, respectively. On the other hand, the concentration for the known antithrombotic agent, $N^2$-(p-tolylsulfonyl)-L-arginine methyl ester, was 1,100 $\mu$ M.

When a solution containing an $N^2$-naphthalenesulfonyl-L-argininamide of this invention was administered intravenously into animal bodies, the high antithrombotic activity in the circulating blood was maintained for from 1 to 3 hours. The halflife for decay of the anti-thrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight. Representative $LD_{50}$ values, for example, for 2-[$N^2$-(6,7-dimethoxy-2-naphthalenesulfonyl)-L-arginyl]-1,2,3,4-tetrahydroisoquinoline-3-carboxylic acid and 2-[$N^2$-(6,7-dimethoxy-2-naphthalenesulfonyl)-L-arginyl]isoindoline-1-carboxylic acid are each more than 1,000 milligrams per kilogram. On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents of this invention may be administered alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

(A)

$N^2$-(6,7-dimethoxy-2-naphthalenesulfonyl)-L-arginyl chloride hydrochloride

A suspension of 2.0 g of $N^2$-(6,7-dimethoxy-2-naphthalenesulfonyl)-L-arginine in 20 ml of thionyl chloride containing a few drops of dimethylformamide was stirred for 2 hours at room temperature.

Addition of cold dry diethyl ether resulted in a precipitate which was collected by filtration and washed several times with dry diethyl ether to give $N^2$-(6,7-dimethoxy-2-naphthalenesulfonyl)-L-arginyl chloride hydrochloride.

(B) Methyl 2-[N²-(6,7-dimethoxy-2-naphthalenesulfonyl)-L-arginyl]-1,2,3,4-tetrahydroisoquinoline-3-carboxylate To a stirred solution of 1.8 g of methyl 1,2,3,4-tetrahydroisoquinoline-3-carboxylate hydrochloride and 8 ml of triethylamine in 50 ml of chloroform which was cooled in an ice bath, there was carefully added N²-(6,7-dimethoxy-2-naphthalenesulfonyl)-L-arginyl chloride hydrochloride obtained above. The reaction mixture was allowed to stand overnight at room temperature. The reaction mixture was washed twice with 50 ml of saturated sodium chloride solution and evaporated to dryness. The residue was dissolved in water-ethanol and ajusted to pH 12 with 5N NaOH solution at a temperature below 0° C to precipitate a solid. This was collected by filtration to give 3 g of methyl 2-[N²-(6,7-dimethoxy-2-naphthalenesulfonyl)-L-arginyl]-1,2,3,4-tetrahydroisoquinoline-3-carboxylate.

I.R. (KBr): 3,350, 1,740, 1,640, 1,260, 1,160 cm⁻¹.

Analysis-Calcd. for $C_{29}H_{35}O_7N_5S_1$ (percent): C, 58.27; H, 5.90; N, 11.72. Found (percent): C, 58.45; H, 6.03; N, 11.53.

(C) 2-[N²-(6,7-dimethoxy-2-naphthalenesulfonyl)-L-arginyl]-1,2,3,4-tetrahydroisoquinoline-3-carboxylic acid A solution of 3 g of methyl 2-[N²-(6,7-dimethoxy-2-naphthalenesulfonyl)-L-arginyl]-1,2,3,4-tetrahydroisoquinoline-3-carboxylate in 15 ml of methanol and 5 ml of 2N NaOH solution was warmed to 50° C and held at that temperature for 15 hours. At the end of this period, the reaction mixture was concentrated and chromatographed on 200 ml of Daiaion ® SK 102 ion exchange resin (200–300 mesh, H⁺ form, manufactured by Mitsubishi Chemical Industries Limited) packed in water, washed with ethanol-water (1:4) and eluted with ethanol-water-NH₄OH (10:9:1). The main fraction was evaporated to dryness and washed with ether to give 1.6 g of 2-[N²-(6,7-dimethoxy-2-naphthalenesulfonyl)-L-arginyl]-1,2,3,4-tetrahydroisoquinoline-3-carboxylic acid.

I.R. (KBr): 3,300 (broad), 1,620, 1,250, 1,150 cm⁻.

Analysis-Calcd. for $C_{28}H_{33}O_7N_5S_1$ (percent): C, 57.62; H, 5.70; N, 12.00. Found (percent): C, 57.68; H, 5.55; N, 11.73.

EXAMPLE 2

(A) Methyl 2-[N^G-nitro-N²-(6,7-dimethoxy-2-naphthalenesulfonyl)-L-arginyl]isoindoline-1-carboxylate To a well stirred solution of 2.5 g of methyl 2-N^G-nitro-L-arginyl)isoindoline-1-carboxylate hydrochloride and 2 ml of triethylamine in 40 ml of chloroform was added in portions 1.5 g of 6,7-dimethoxy-2-naphthalenesulfonyl chloride. The reaction mixture was stirred overnight at room temperature. At the end of this period, the chloroform solution was washed consecutively with 5% HCl, saturated NaCl, saturated NaHCO₃ and saturated NaCl solutions. The chloroform solution was evaporated and the residue was chromatographed on silica gel packed in chloroform, and eluted from chloroform containing 3% ethanol. The main fraction was evaporated to dryness to give 1.3 g of methyl 2-[N^G-nitro-N²-(6,7-dimethoxy-2-naphthalenesulfonyl)-L-arginyl]isoindoline-1-carboxylate.

(B) 2-[N²-(6,7-dimethoxy-2-naphthalenesulfonyl)-L-arginyl]isoindoline-1-carboxylic acid To a solution of 1.0 g of methyl 2-[N^G-nitro-N²-(6,7-dimethoxy-2-naphthalenesulfonyl)-L-arginyl]isoindoline-1-carboxylate in 20 ml of tert-butanol and 3 ml of acetic acid was added 0.4 g of palladium black and then the mixture was shaken in a hydrogen atmosphere for 15 hours at room temperature. The solution was filtered to remove the catalyst and evaporated to give an oily product.

The residue was dissolved in 10 ml of methanol and 3 ml of 2N NaOH solution. The solution was warmed to 50° C and held at that temperature for 15 hours. At the end of this period, the reaction mixture was evaporated to dryness. The residue was chromatographed on 300 ml of Daiaion ® SK 102 ion exchange resin (100–200 mesh, H⁺ form, manufactured by Mitsubishi Chemical Industries Limited) packed in water, washed with 50% ethanol-water and eluted with ethanol-water-NH₄OH (5:4:1). The main fraction was evaporated to dryness to give a gummy material. This was recrystallized from ethanol-water to give 0.7 g of 2-[N²-(6,7-dimethoxy-2-naphthalenesulfonyl)-L-arginyl]isoindoline-1-carboxylic acid in the form of a powder.

I.R. (KBr): 3,360, 1,625, 1,260, 1,150 cm⁻¹.

Analysis-Calcd. for $C_{27}H_{31}O_7N_5S_1$ (percent): C, 56.93; H, 5.49; N, 12.30. Found (percent): C, 57.12; H, 5.43; H, 12.14.

The following compounds and their esters, such as methyl, ethyl or benzyl ester are prepared in a similar manner:

2-[N²-(5-chloro-1-naphthalenesulfonyl)-L-arginyl]-1,2,3,4-tetrahydroisoquinoline-3-carboxylic acid 1-[N²-(5-hydroxy-1-naphthalenesulfonyl)-L-arginyl]-1,2,3,4-tetrahydroquinoline-2-carboxylic acid 1-[N²-(5-nitro-1-naphthalenesulfonyl)-L-arginyl]indoline-2-carboxylic acid 2-[N²-(5-cyano-1-naphthalenesulfonyl)-L-arginyl]isoindoline-1-carboxylic acid 2-[N²-(7-methyl-2-naphthalenesulfonyl)-L-arginyl]-1,2,3,4-tetrahydroisoquinoline-3-carboxylic acid 2-[N²-(7-methyl-2-naphthalenesulfonyl)-L-arginyl]isoindoline-1-carboxylic acid 2-[N²-(6,7-dimethyl-2-naphthalenesulfonyl-L-arginyl]isoindoline-1-carboxylic acid 2-[N²-(7-methoxy-2-naphthalenesulfonyl)-L-arginyl]-1,2,3,4-tetrahydroisoquinoline-1-carboxylic acid 2-[N²-(7-methoxy-2-naphthalenesulfonyl)-L-arginyl]isoindoline-1-carboxylic acid 2-[N²-(4,6-dimethoxy-2-naphthalenesulfonyl)-L-arginyl]-1,2,3,4-tetrahydroisoquinoline-3-carboxylic acid 2-[N²-(5-methoxy-1-naphthalenesulfonyl)-L-arginyl]isoindoline-1-carboxylic acid 2-[N²-(5-ethoxy-1-naphthalenesulfonyl)-L-arginyl]-1,2,3,4-tetrahydroisoquinoline-3-carboxylic acid 2-[N²-(5-dimethylamino-1-naphthalenesulfonyl)-L-arginyl]isoindoline-1-carboxylic acid 2-[N²-(1-naphthalenesulfonyl)-L-arginyl]-1,2,3,4-tetrahydroisoquinoline-3-carboxylic acid 2-[N²-(2-naphthalenesulfonyl)-L-arginyl]isoindoline-1-carboxylic acid 2-[N²-(5,6,7,8-tetrahydro-2-naphthalenesulfonyl)-L-arginyl]-1,2,3,4-tetrahydroisoquinoline-3-carboxylic acid 2-[N²-(5,6,7,8-tetrahydro-1-naphthalenesulfonyl)-L-arginyl]isoindoline-1-carboxylic acid

EXAMPLE 3

Tablets Suitable for Oral Administration

Tablets containing the ingredients indicated below may be prepared by conventional techniques.

| Ingredient | Amount per tablet (mg) |
| --- | --- |
| 2-[N²-(6,7-dimethoxy-2-naphthalene-sulfonyl)-L-arginyl]isoindoline-1-carboxylic acid | 250 |
| Lactose | 140 |
| Corn starch | 35 |
| Talcum | 20 |
| Magnesium stearate | 5 |
| Total | 450 mg |

EXAMPLE 4

Capsules for Oral Administration

Capsules of the below were made up by thoroughly mixing together batches of the ingredients and filling hard gelatin capsules with the mixture.

| Ingredient | Amount per capsule (mg) |
| --- | --- |
| 2-[N²-(6,7-dimethoxy-2-naphthalene-sulfonyl)-L-arginyl]isoindoline-1-carboxylic acid | 250 |
| Lactose | 250 |
| Total | 500 mg |

EXAMPLE 5

Sterile Solution for Infusion

The following ingredients are dissolved in water for intravenous perfusion and the resulting solution is then sterilized.

| Ingredients | Amount (g) |
| --- | --- |
| 2-[N²-(6,7-dimethoxy-2-naphthalenesulfonyl)-L-arginyl]-1,2,3,4-tetrahydroisoquinoline-3-carboxylic acid | 25 |
| Buffer system | As desired |
| Glucose | 25 |
| Distilled water | 500 |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. N²-naphthalenesulfonyl-L-argininamides having the formula

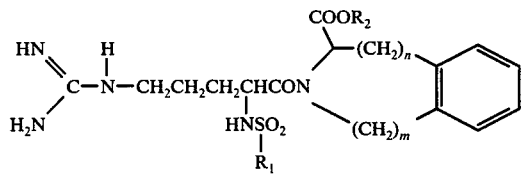

and the pharmaceutically acceptable salts thereof, wherein $R_1$ is selected from the group consisting of naphthyl, 5,6,7,8-tetrahydronaphthyl and naphthyl substituted with at least one substituent selected from the group consisting of halo, nitro, cyano, hydroxy, $C_1$–$C_{10}$ alkyl, $C_1$–$C_{10}$ alkoxy and $C_2$–$C_{20}$ dialkylamino; $R_2$ is selected from the group consisting of hydrogen, $C_1$–$C_{10}$ alkyl, $C_6$–$C_{10}$ aryl and $C_7$–$C_{12}$ aralkyl; $m$ is an integer of 0, 1 or 2; $n$ is an integer of 0, 1 or 2; and $m + n$ is an integer of 1 or 2.

2. The compound of claim 1, wherein $R_1$ is selected from the group consisting of naphthyl, 5,6,7,8-tetrahydronaphthyl and naphthyl substituted with at least one substituent selected from the group consising of halo, hydroxy, $C_1$–$C_5$ alkyl, $C_1$–$C_5$ alkoxy and $C_2$–$C_{10}$ dialkylamino; $R_2$ is selected from the group consisting of hydrogen, $C_1$–$C_6$ alkyl, phenyl and $C_7$–$C_{10}$ aralkyl.

3. The compound of claim 2, wherein $R_1$ is selected from the group consisting of 1-naphthyl, 2-naphthyl, 5,6,7,8-tetrahydro-1-naphthyl, 5,6,7,8-tetrahydro-2-naphthyl, 6-methyl-2-naphthyl, 6-methyl-1-naphthyl, 7-methyl-1-naphthyl, 7-methyl-2-naphthyl, 6-ethyl-2-naphthyl, 6,7-dimethyl-1-naphthyl, 6,7-dimethyl-2-naphthyl, 6-isopropyl-2-naphthyl, 5-chloro-1-naphthyl, 6-chloro-2-naphthyl, 6-bromo-1-naphthyl, 5-hydroxy-1-naphthyl, 7-hydroxy-2-naphthyl, 5-dimethylamino-1-naphthyl, 5-dimethylamino-2-naphthyl, 5-diethylamino-1-naphthyl, 6-dimethylamino-1-naphthyl, 6-dimethylamino-2-naphthyl, 5-methoxy-1-naphthyl, 6-methoxy-2-naphthyl, 7-methoxy-2-naphthyl, 4,6-dimethoxy-2-naphthyl, 6,7-dimethoxy-2-naphthyl and 6,7-diethoxy-2-naphthyl; and $R_2$ is hydrogen, methyl, ethyl or tert-butyl.

4. The compound of claim 3, wherein $R_2$ is hydrogen.

5. The compound of claim 3, wherein $m$ is 1 and $n$ is 1.

6. The compound of claim 3, wherein $m$ is 1 and $n$ is 0.

7. A compound of claim 4, which is 2-[N²-(6,7-dimethoxy-2-naphthalenesulfonyl)-L-arginyl]-1,2,3,4-tetrahydroisoquinoline-3-carboxylic acid.

8. A compound of claim 4, which is 2-[N²-(6,7-dimethoxy-2-naphthalenesulfonyl)-L-arginyl]isoindoline-1-carboxylic acid.

9. A compound of claim 4, which is 2-[N²-(7-methoxy-2-naphthalenesulfonyl)-L-arginyl]isoindoline-1-carboxylic acid.

10. A compound of claim 4, which is 2-[N²-(7-methyl-2-naphthalenesulfonyl)-L-arginyl]isoindoline-1-carboxylic acid.

11. A method for inhibiting activity and suppressing activation of thrombin in vivo, which comprises administering to a patient a pharmaceutically effective amount of an N²-naphthalenesulfonyl-L-argininamide having the formula

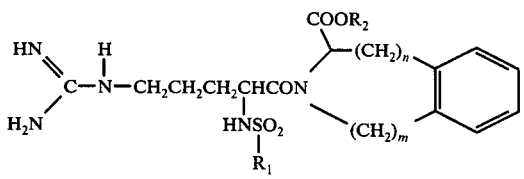

or the pharmaceutically acceptable salt thereof, wherein $R_1$ is selected from the group consisting of naphthyl, 5,6,7,8-tetrahydronaphthyl and naphthyl substituted with at least one substituent selected from the group consisting of halo, nitro, cyano, hydroxy, $C_1$–$C_{10}$ alkyl, $C_1$–$C_{10}$ alkoxy and $C_2$–$C_{20}$ dialkylamino; $R_2$ is selected from the group consisting of hydrogen, $C_1$–$C_{10}$ alkyl, $C_6$–$C_{10}$ aryl and $C_7$–$C_{12}$ aralkyl, $m$ is an integer of 0, 1 or 2; $n$ is an integer of 0, 1 or 2; and $m + n$ is an integer of 1 or 2.

12. A pharmaceutical composition which comprises an antithrombotically effective amount of a compound of claim 1 and a pharmaceutically acceptable adjuvant.

* * * * *